(12) United States Patent
Fujioka

(10) Patent No.: US 8,992,500 B2
(45) Date of Patent: Mar. 31, 2015

(54) FASTENING TAPE AND DISPOSABLE DIAPER HAVING THE SAME, AND PROCESS FOR MANUFACTURING THEREFOR

(75) Inventor: Masaru Fujioka, Mima-gun (JP)

(73) Assignee: Livedo Corporation, Ehime (JP)

( * ) Notice: Subject to any disclaimer, the term of this patent is extended or adjusted under 35 U.S.C. 154(b) by 943 days.

(21) Appl. No.: 12/935,104

(22) PCT Filed: Mar. 25, 2009

(86) PCT No.: PCT/JP2009/056787
§ 371 (c)(1),
(2), (4) Date: Sep. 28, 2010

(87) PCT Pub. No.: WO2009/123253
PCT Pub. Date: Oct. 8, 2009

(65) Prior Publication Data
US 2011/0015608 A1    Jan. 20, 2011

(30) Foreign Application Priority Data

Mar. 31, 2008   (JP) ................. 2008-093509

(51) Int. Cl.
*A61F 13/15*        (2006.01)
*A61F 13/56*        (2006.01)
*A61F 13/62*        (2006.01)

(52) U.S. Cl.
CPC ....... *A61F 13/5622* (2013.01); *A61F 13/15731* (2013.01); *A61F 13/15756* (2013.01); *A61F 13/62* (2013.01); *A61F 13/622* (2013.01); *Y10T 428/24017* (2015.01)
USPC ............ 604/391; 604/396; 604/386; 604/389

(58) Field of Classification Search
USPC .................................. 604/391, 396, 386, 389
See application file for complete search history.

(56) References Cited

U.S. PATENT DOCUMENTS

| | | | | |
|---|---|---|---|---|
| 4,973,326 A | * | 11/1990 | Wood et al. | 604/391 |
| 6,030,373 A | * | 2/2000 | VanGompel et al. | 604/391 |
| 6,770,065 B1 | * | 8/2004 | Sasaki et al. | 604/391 |

FOREIGN PATENT DOCUMENTS

| | | |
|---|---|---|
| JP | 2001-87308 A | 4/2001 |
| JP | 2002-045214 A | 2/2002 |
| JP | 2003-159279 A | 6/2003 |
| JP | 2005-245902 A | 9/2005 |

(Continued)

OTHER PUBLICATIONS

International Search Report for PCT Patent App. No. PCT/JP2009/056787 (Jun. 30, 2009).

(Continued)

*Primary Examiner* — Jacqueline F. Stephens
(74) *Attorney, Agent, or Firm* — Cermak Nakajima & McGowan LLP; Tomoko Nakajima

(57) ABSTRACT

A fastening tape comprising a tab portion formed at one end of a tape substrate made of a nonwoven fabric, and a fixing portion formed at the other end of the tape substrate so as to be attached to a disposable diaper, wherein: a male component of a hook-and-loop fastener is fixed to a surface of the tape substrate at the tab portion; the opposite surface of the surface with the male component of the tape substrate is embossed; the tab portion is folded back at the boundary between the tab portion and the fixing portion so that the male component is on the folded inner side; and the male component on the tab portion is joined to the fixing portion of the tape substrate.

18 Claims, 7 Drawing Sheets

(56) References Cited

FOREIGN PATENT DOCUMENTS

| JP | 2005-279005 A | 10/2005 |
| JP | 2005-296603 A | 10/2005 |
| JP | 2005-312707 A | 11/2005 |

OTHER PUBLICATIONS

Invitation to Respond to Written Opinion for Singapore Patent App. No. 201006642-1 (Aug. 10, 2011).

First Notification of Office Action for China Patent App. No. 200980109688.4 (Aug. 31, 2012) with English language translation.
Notice of Reasons for Rejection for Japanese Patent App. No. 2008-093509 (Oct. 2, 2012) with English translation thereof.
Extended European Search Report for EP Patent App. No. 09728202.4 (Mar. 19, 2013).
Office Action from Malaysian Patent App. No. PI2010004004 (Oct. 31, 2013).
Office Action from Taiwan Patent App. No. 98110082 (Sep. 29, 2014).

* cited by examiner

FASTENING TAPE AND DISPOSABLE DIAPER HAVING THE SAME, AND PROCESS FOR MANUFACTURING THEREFOR

This application is a national phase entry under 35 U.S.C. §371 of PCT Patent Application No. PCT/JP2009/056787, filed on Mar. 25, 2009, which claims priority under 35 U.S.C. §119 to Japanese Patent Application No. 2008-093509, filed Mar. 31, 2008, both of which are incorporated by reference.

TECHNICAL FIELD

The present invention relates to a fastening tape and a disposable diaper having the fastening tape. The present invention also relates to a process for manufacturing the fastening tape and a process for manufacturing the disposable diaper having the fastening tape.

BACKGROUND ART

Conventionally, there is a disposable diaper that utilizes a hook-and-loop fastener including a male component (a hook fastener) and a female component (a loop fastener) as a fastening tape to fit the disposable diaper to a wearer. Since the hook-and-loop fastener can be used for joining and releasing repeatedly, the disposable diaper with the hook-and-loop fastener is easily adjusted a fastening position in wearing and is easily looked inside of the diaper when the diaper is worn.

As a disposable diaper with the hook-and-loop fastener, Japanese Laid-Open Patent Publication No. 2001-87308 discloses a disposable diaper in which a male component of a fastening tape is temporarily joined to a top sheet by folding back the fastening tape with the male component on the top sheet so that the male component faces to the top sheet, and locally-pressing the corresponding part of the folded back fastening tape which the male component is located so that the male component of the fastening tape is not released from a disposable diaper main body during manufacturing. Also, Japanese Laid-Open Patent Publication No. 2002-45214 discloses a fastening tape in which a male component is fixed to a folded back segment formed at one end of a substrate sheet made of a nonwoven fabric that can join to the male component. According to the fastening tape disclosed in the publication No. 2002-45214, the folded back segment is folded back, allowing the male component to be temporarily joined to the nonwoven fabric of the substrate sheet.

DISCLOSURE OF INVENTION

Technical Problem

Although the above publications disclose a technique for preventing the fastening tape from joining to other components before using the fastening tape, nothing is described about a technique for preventing the fastening tape from rejoining itself when the fastening tape is folded back during use. The above publications do not describe usage of an embossed substrate sheet for the fastening tape. Furthermore, the disposable diaper disclosed in the Publication No. 2001-87308 has a problem that the top sheet is damaged or the male component is crushed, because the top sheet is locally-pressed together with the male component when the male component of the fastening tape is temporarily joined.

The present invention has been achieved in view of the above circumstances, and an object of the present invention is to provide a fastening tape that hardly rejoins itself when the fastening tape is folded back during use, though the fastening tape is temporarily joined before using the fastening tape; a disposable diaper that has the fastening tape; and a manufacturing method for these.

Technical Solution

The present invention, which has solved the above problem, provides a fastening tape comprising a tab portion formed at one end of a tape substrate made of a nonwoven fabric, and a fixing portion formed at the other end of the tape substrate so as to be attached to a disposable diaper, wherein: a male component of a hook-and-loop fastener is fixed to a surface of the tape substrate at the tab portion; the opposite surface of the surface with the male component of the tape substrate is embossed; the tab portion is folded back at the boundary between the tab portion and the fixing portion so that the male component is on the folded inner side; and the male component on the tab portion is joined to the fixing portion of the tape substrate. The fastening tape of the present invention allows temporary joining of the fastening tape without damaging a disposable diaper main body since the male component on the tab portion joins the fixing portion of the tape substrate. In addition, since the opposite surface of the surface with the male component of the tape substrate is embossed, shallow convexoconcaves are formed on the surface with the male component of the tape substrate, resulting in allowing the male component on the tab portion to join the tape substrate at the fixing portion when the tab portion is folded back at the boundary between the tab portion and the fixing portion so that the male component is on the inner side. However, since such shallow convexoconcaves have a weak engaging force against the male component, once a joining to the male component is released, the fastening tape hardly rejoins itself when the fastening tape is folded back in wearing the disposable diaper or using the fastening tape.

For the fastening tape of the present invention, the surface with the male component of the tape substrate is preferably not embossed. The fastening tape that the surface with the male component of the tape substrate is not embossed hardly rejoins itself in wearing the disposable diaper or using the fastening tape.

The tape substrate of the fastening tape of the present invention is preferably made of a spunbond nonwoven fabric having a weight per unit area in the range of from 30 g/m² to 100 g/m². Using such a nonwoven fabric easily gives the nonwoven fabric breathability and elasticity. Therefore, the fastening tape made of the nonwoven fabric is gentle to the skin, improves comfort for the wearer, and does not easily bend to improve a handling.

For the fastening tape of the present invention, the male component on the tab portion is preferably joined to the fixing portion by pressing the whole area of the male component against the fixing portion. The engaging force between the male component and the surface which the male component is fixed to of the tape substrate is increased by pressing the whole area of the male component against the fixing portion, resulting in hooking and temporary joining of the male component to the fixing portion. Further, the damage of the male component due to locally and firmly pressing the male component can be prevented. Still further, damage to the surface which the male component is joined of the tape substrate is also prevented, resulting in an excellent feel of the surface against the wearer's skin.

The present invention provides a process for manufacturing a fastening tape comprising the steps of supplying a tape substrate made of a nonwoven fabric having one embossed surface; fixing a male component of a hook-and-loop fastener on the other surface of the tape substrate; folding back the tape substrate so that the male component is on the inner side; and pressing the whole area of the folded back male component to join the male component to the facing nonwoven fabric of the tape substrate. The present invention also provides a process for manufacturing a fastening tape comprising the steps of embossing one surface of a tape substrate made of a nonwoven fabric; fixing a male component of a hook-and-loop fastener on the other surface of the tape substrate; folding back the tape substrate so that the male component is on the inner side; and pressing the whole area of the folded back male component to join the male component to the facing nonwoven fabric of the tape substrate. According to such processes for manufacturing, the fastening tape of the present invention is manufactured appropriately.

In the processes for manufacturing of the present invention, for joining the male component to the facing nonwoven fabric of the tape substrate, the whole area of the folded back male component is preferably pressed by a roll, and more preferably pressed by a flat roll and an embossing roll, and even more preferably pressed by a flat roll and a knurly embossing roll.

In addition, the present invention also discloses a disposable diaper having a front portion, a back portion and a crotch portion therebetween, the disposable diaper comprising the fastening tape attached to a side edge portion of the front or the back portion; and a process for manufacturing thereof.

Advantageous Effects

The fastening tape and the disposable diaper of the present invention hardly rejoins itself when the fastening tape is folded back during use, though the fastening tape is temporarily joined before using the fastening tap.

Further, according to the process for manufacturing a fastening tape and a disposable diaper of the present invention, the fastening tape and the disposable diaper of the present invention can be manufactured appropriately.

BRIEF DESCRIPTION OF DRAWINGS

FIG. 1A shows a plain view, FIG. 1B shows a view in which a tab portion in FIG. 1A shows extended out, FIG. 1C shows a cross sectional view along line A-A in FIG. 1A, and FIG. 1D shows a cross sectional view along line B-B in FIG. 1B.

EXPLANATION OF REFERENCE

Figure 1:
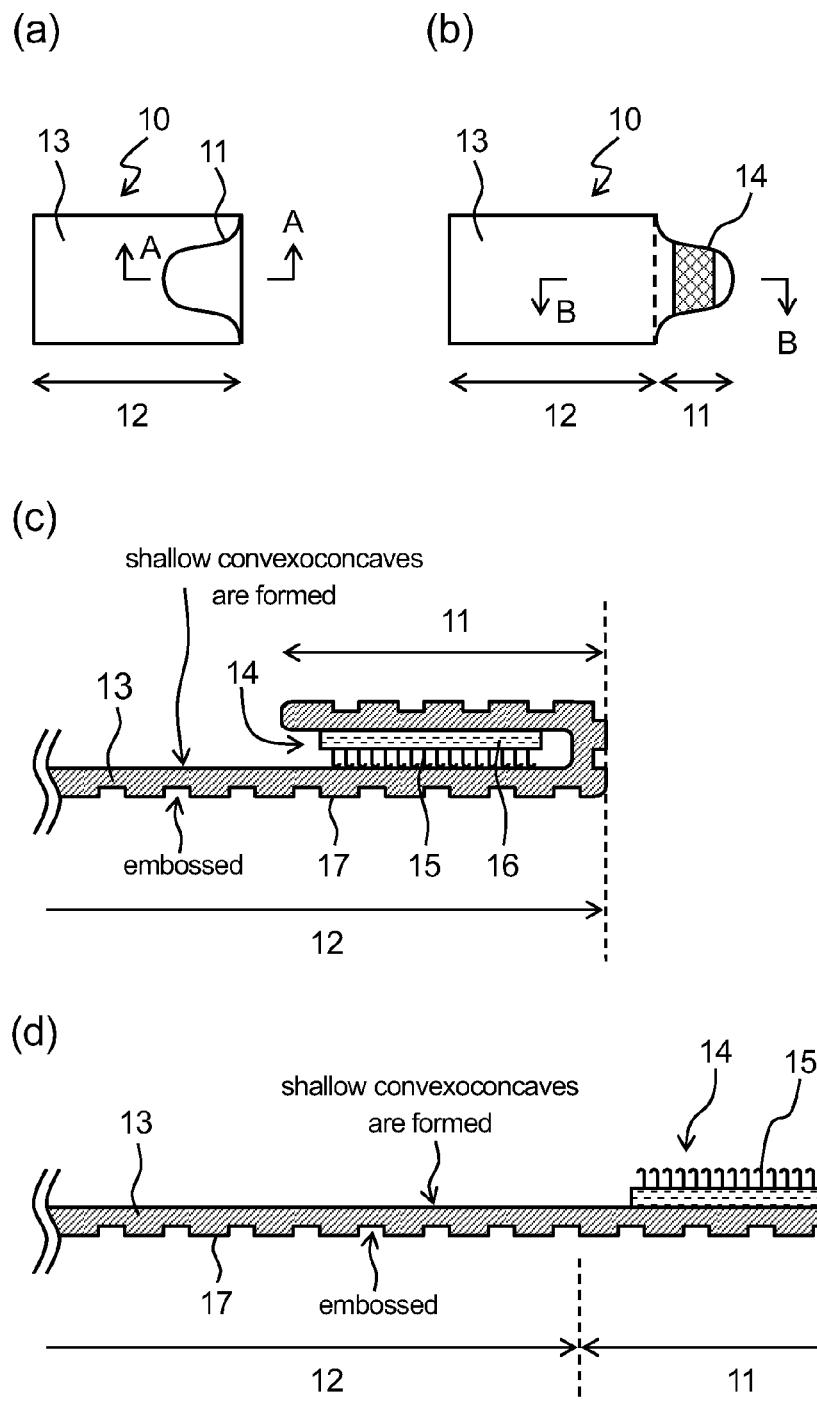
FIGS. 1A-1D show an example of a fastening tape of the present invention.

1: a disposable diaper
2: a top sheet
3: a back sheet
4: an absorbent core
5: a side sheet
6: a fastener receiving part
10: a fastening tape
11: a tab portion
12: a fixing portion
13: a tape substrate
14: a male component
30: knurly embossings
34: an embossing roll

DESCRIPTION OF ENBODIMENTS

First, a fastening tape of the present invention is explained. The fastening tape of the present invention comprises a tab portion formed at one end of a tape substrate and a fixing portion formed at the other end of the tape substrate.

The tab portion is formed at one end of the tape substrate and is a part that a male component of a hook-and-loop fastener is fixed. The male component of the hook-and-loop fastener is fixed to one surface of the tab portion of the tape substrate. The male component has hooks of, for example, an anchor shape, a hook shape, a mushroom shape, or the like.

The fixing portion is formed at the other end of the tape substrate of the tape substrate and is a part that is to be attached to a disposable diaper main body. The fixing portion is fixed to the disposable diaper main body by, for example, an adhesive, heat bonding, or ultrasonic bonding. Also, the fixing portion is a part which the male component of the tab portion is joined when the tab portion is folded back at the boundary between the tab portion and the fixing portion so that the male component is on the folded inner side.

The tab portion and the fixing portion are divided by folding back at the boundary of them when the male component on the tab portion joins the fixing portion of the tape substrate.

The shape of the fastening tape and the shape of the tab portion and the fixing portion are not particularly limited. The shape of the fastening tape may be, for example, polygonal such as rectangular, oval, or the like. However, an elongated shape is preferable. The tab portion may be formed in such a manner that one end of the tape substrate has, for example, a linear or meandering outline. The fixing portion may also be formed in such a manner that the other end of the tape substrate of the tape substrate has a linear or meandering outline. In the present invention, the tab portion is preferably formed in such a manner that one end of the tape substrate has a meandering outline in view of a manufacturing efficiency.

Sizes of the tab portion and the fixing portion are not particularly limited. However, a length of the tab portion is preferably shorter than that of the fixing portion. The reason is described later. The lengths of the tab portion and the fixing portion are defined as lengths in direction that are perpendicular to a folded-back line formed at the boundary between the tab portion and the fixing portion and are on the same surface as the tape substrate.

The tab portion is folded back at the boundary between the tab portion and the fixing portion so that the male component is on the inner side, and the male component on the tab portion joins the fixing portion of the tape substrate. When using the fastening tape, the male component on the tab portion is exposed by releasing the join of the male component on the tab portion of the tape substrate and spreading out the folded tab portion.

Prior to the usage of the fastening tape, the male component on the tab portion joins preferably only the fixing portion of the tape substrate. For realizing this embodiment, the length of the tab portion may be set to be shorter than that of the fixing portion, for example. The lengths of the tab portion and the fixing portion are defined as lengths in direction that are perpendicular to the folded-back line formed at the boundary between the tab portion and the fixing portion and are on the same surface as the tape substrate. In the case that the male component on the tab portion joins only the fixing portion of the tape substrate prior to the usage of the fastening tape, the male component does not join the disposable diaper main body. In this case, the male component does not damage a sheet of the disposable diaper main body which faces to a wearer, such as a top sheet or a side sheet, resulting in an excellent feel of the top sheet and the side sheet against the wearer's skin.

A material used for the tape substrate made of a nonwoven fabric includes a nonwoven fabric, a laminate of a nonwoven fabric and a plastic film, a laminate in which a plastic film interposed between nonwoven fabrics, and the like. The tape substrate made of a nonwoven fabric preferably has at least a nonwoven fabric surface which the male component is fixed to. This is because the nonwoven fabric surface with the male component of the tape substrate allows easy joining of the male component to the tape substrate. For example, when a composite material which is a laminate of a nonwoven fabric and a plastic film is used, the nonwoven fabric surface is preferably the surface which the male component is fixed to. Further, more preferably, both the surface with the male component and the opposite surface thereof are made of a nonwoven fabric. Still further, the tape substrate is even more preferably made of only a nonwoven fabric in view of easy manufacturing of the fastening tape.

A nonwoven fabric used for the tape substrate is preferably a nonwoven fabric manufactured by a spunbond method, an air-through method, a point bonding method, a melt blowing method, an airlaid method, a combination of these methods, or the like. Further, a nonwoven fabric manufactured by the spunbond method or a SMS method which is a combination of the spunbond method and the melt blowing method is preferable, and a nonwoven fabric manufactured by the spunbond method is especially preferable. By using such nonwoven fabrics, the tape substrate with high strength is easily obtained.

A material of the nonwoven fabric is chosen from synthetic fibers such as polypropylene, polyethylene, polyester, polyamide, and the like; natural fibers such as pulp, silk, and the like, appropriately. Among them, synthetic fibers such as polypropylene, polyethylene, polyester, and the like are preferable; a polypropylene fiber or a polyester fiber is more preferable; and a polypropylene fiber is even more preferable. By using nonwoven fabrics obtained from such materials, a tape substrate with high strength is easily obtained.

The nonwoven fabric has preferably a weight per unit area of 30 $g/m^2$ or more, more preferably 50 $g/m^2$ or more, preferably 100 $g/m^2$ or less, and more preferably 85 $g/m^2$ or less. Using the nonwoven fabric having a weight per unit area in the range of from 30 $g/m^2$ to 100 $g/m^2$ easily gives the nonwoven fabric breathability and elasticity. When the nonwoven fabric having a weight per unit area in the range of from 30 $g/m^2$ to 100 $g/m^2$ is used, breathability of the nonwoven fabric is easily ensured and elasticity of the nonwoven fabric is easily obtained. Therefore, the fastening tape made of such a nonwoven fabric is gentle to the skin, improves comfort for the wearer, and does not easily bend to improve a handling.

Thus, as the material used for the tape substrate, a spunbond nonwoven fabric having a weight per unit area in the range of from 30 $g/m^2$ to 100 $g/m^2$ is especially preferable, and a spunbond nonwoven fabric having a weight per unit area in the range of from 50 $g/m^2$ to 85 $g/m^2$ is most preferable.

In the present invention, the opposite surface of the surface provided with the male component of the tape substrate is preferably embossed. The embossing is conducted preferably by hot embossing. In the present invention, shallow convexoconcaves are preferably formed on the surface with the male component of the tape substrate by embossing the opposite surface of the surface with the male component of the tape substrate. Forming the shallow convexoconcaves on the surface with the male component of the tape substrate allows the male component on the tab portion to join the tape substrate at the fixing portion when the tab portion is folded back at the boundary between the tab portion and the fixing portion so that the male component is on the inner side. However, since such shallow convexoconcaves have a weak engaging force against the male component, once a joining with the male component is released, the fastening tape hardly rejoins itself when the fastening tape is folded back in using the fastening tape.

On the other hand, the surface provided with the male component of the tape substrate is preferably not embossed. In the present invention, the surface which the male component is fixed to of the tape substrate is also the surface that the male component is engaged with the fixing portion of the tape substrate to be temporarily joined by folding back the tab portion. In a nonwoven fabric, generally, the surface that is not embossed tends to have a very weak engaging force against a male component, and further, even the shallow convexoconcaves formed surface with the male component of the tape substrate also tends to have a weak engaging force against a male component. Therefore, in the present invention, once the temporary joining of the male component to the fixing portion of the tape substrate is released, the fastening tape hardly rejoins itself when the tab portion folds back, resulting in better handling of the fastening tape. Furthermore, in the case that the male component is disposed such that the male component does not cover the end part of the tab portion, when the nonwoven fabric of the end part folds back, the folded back end part hardly joins the male component, resulting in a lesser possibility of reducing a joining area of the male component.

Here, the temporary joining means joining of the male component of the fastening tape to a predetermined place prior the usage of the diaper in order to prevent the male component of the fastening tape from scratching or damaging other components of the diaper. In the present invention, it is preferable to increase the engaging force between the male component and the surface which the male component is fixed to of the tape substrate by pressing the whole area of the male component against the fixing portion, resulting in hooking and temporary joining of the male component to the fixing portion. In addition, the damage of the male component due to locally and firmly pressing the male component can be prevented, and further, damage to the surface which the male component is joined of the tape substrate is also prevented, resulting in an excellent feel of the surface against the wearer's skin. Details of the method for pressing the male component against the fixing portion are described later.

Embossing is a process of pressing a mold that has convexoconcaves on a surface against a fabric surface. In the present invention, an embossed surface is a surface that has been directly contacted and pressed by a mold which has convexoconcaves on a surface, and as a result, convexoconcaves are preferably formed on the surface. Thus, the opposite surface of the embossed surface having been directly contacted by a mold of a convexoconcaves surface is deemed not to be embossed even if convexoconcaves are also formed on the opposite surface by the effect of embossing of the embossed surface.

An example of the fastening tape of the present invention is explained, referring to FIGS. 1A-1D and FIGS. 2A-2B.

FIG. 1A shows an example of the fastening tape of the present invention, and FIG. 1C shows a cross sectional view along line A-A of FIG. 1A. A fastening tape 10 comprises a tab portion 11 formed at one end of a tape substrate 13 and a fixing portion 12 formed at the other end of the tape substrate 13.

FIG. 1B shows a spread state of the fastening tape 10 shown in FIG. 1A in which the joining of a male component 14 to the tape substrate 13 is released, and FIG. 1D shows a cross sectional view along line B-B of FIG. 1B. When the joining of the male component 14 to the tape substrate 13 of the fastening tapes 10 shown in FIG. 1A and FIG. 1C is released and the tab portion 11 is spread out, the fastening tapes 10 becomes states shown in FIG. 1B and FIG. 1D.

The male component 14 of the hook-and-loop fastener is fixed to a surface of the tape substrate 13 at the tab portion 11. The male component 14 comprises a base part 16 and a hook part 15, and the hook part 15 is composed of a plurality of hooks projected from one surface of the base part 16. The opposite surface of the surface with the hook part 15 of the base part 16 is fixed to the tape substrate 13. The tab portion 11 is folded back at the boundary between the tab portion 11 and the fixing portion 12 so that the male component 14 is on the folded inner side, and the male component 14 on the tab portion 11 is joined to the fixing portion 12 of the tape substrate 13. The opposite surface 17 of the surface with the male component 14 of the tape substrate 13 is embossed, while the surface with the male component 14 of the tape substrate 13 is not embossed.

Figure 2A:
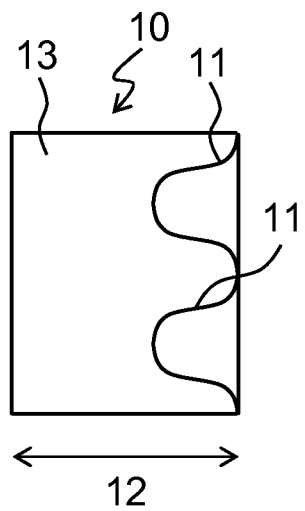
FIGS. 2A and 2B shows an alternative example of a fastening tape of the present invention.
Figure 2B:
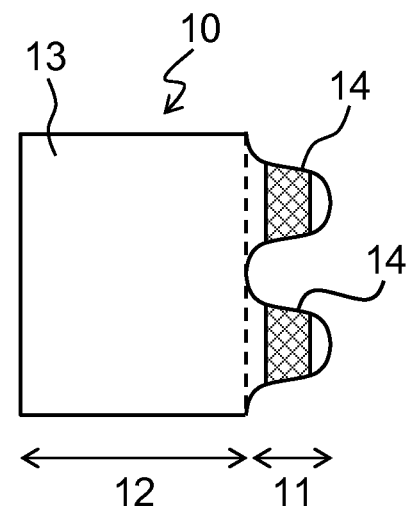

FIG. 2A shows an alternative example of the fastening tape of the present invention. Likewise, in FIG. 2A, the male component 14 on the tab portion 11 joins the fixing portion 12 of the tape substrate 13. FIG. 2B shows a spread state of the fastening tape 10 shown in FIG. 2A in which the joining of the male component 14 to the tape substrate 13 is released and the tab portion 11 is spread out. In FIGS. 2A-2B, one end of the tape substrate 13 has a meandering outline with more meandering numbers than in FIGS. 1A-1D and has two sites where the male components 14 of the tab portion 11 are fixed. The fastening tape shown in FIGS. 2A-2B is preferable, because the male components 14 of the tab portion 11 are fixed on two sites and a wearer easily adjust the size around a waist and a trunk so as to fit the body shape of the wearer in wearing a diaper.

Next, a disposable diaper provided with the fastening tape of the present invention is explained. The disposable diaper of the present invention has a front portion, a back portion and a crotch portion therebetween; and the fastening tape is attached to a side edge portion of the front or the back portion. Here, when the disposable diaper is worn, the part applied to the abdomen side of the wearer is called the front portion, the part applied to the buttocks side of the wearer is called the back portion, and the part positioned between the front portion and the back portion and applied to the crotch of the wearer is called the crotch portion.

In the present invention, an object that is formed of a front portion, a back portion and a crotch portion therebetween, and has an absorbent core may be called a disposable diaper main body. The disposable diaper main body includes, for example, a laminate comprising a liquid-permeable top sheet, a liquid-impermeable back sheet and an absorbent core interposed therebetween; the laminate having a front portion, a back portion and a crotch portion therebetween. The disposable diaper main body also includes an object comprising an outer pants sheet having a front portion, a back portion and a crotch portion therebetween; and an absorbent main body comprising a liquid-permeable top sheet, a liquid-impermeable back sheet and an absorbent core interposed therebetween, and disposed on the surface of a wearer's side of the outer pants sheet.

The fastening tape is attached to the disposable diaper by joining the fixing portion of the tape substrate to the disposable diaper main body. The fixing portion of the tape substrate, for example, may be joined to between two components constituting the disposable diaper main body, or may be joined to one surface of a component constituting the disposable diaper main body. The fixing portion of the tape substrate is joined to, for example, between a top sheet and a back sheet, between a side sheet and a back sheet, or one surface of an outer pants sheet.

The fastening tape is attached to at least one part selected from the group consisting of the left side edge portion of the front portion, the right side edge portion of the front portion, the left side edge portion of the back portion, and the right side edge portion of the back portion of the disposable diaper. Preferably, a pair of fastening tapes is attached to the left and the right side edge portions of the front portion, or the left and the right side edge portions of the back portion.

The disposable diaper of the present invention is preferably provided with a fastener receiving part. The fastener receiving part is a part or a component that can join the male component of the fastening tape. For example, when the fastening tape is attached to the front portion, the fastener receiving part is preferably disposed at the back portion of the disposable diaper. Also, when the fastening tape is attached to the back portion, the fastener receiving part is preferably disposed at the front portion of the disposable diaper.

The fastening tape is preferably attached to the disposable diaper so that the surface with the male component of the fastening tape faces a wearer's side. In this case, since the non-embossed surface of the tape substrate faces the wearer, a rough feel of the tape substrate against the wearer reduces, resulting in an excellent feel against the wearer's skin. In this case, the fastener receiving part is preferably disposed on the outer surface of the disposable diaper, which is the opposite surface of the surface which faces the wearer.

Thus, for the disposable diaper of the present invention, a pair of fastening tapes is preferably attached to the left and the right side edge portions of the front or back portion so that the surface with the male component of the fastening tape faces a wearer, and the fastener receiving part is preferably disposed on the outer surface of the back or front portion of the disposable diaper. By arranging the fastening tape and the fastener receiving part in this manner, the adjustable range of the diaper to the size around a wearer's waist can be expanded as described later.

To wear the disposable diaper of the present invention, the male component of the fastening tape attached to the back portion is joined to the fastener receiving part disposed at the front portion, or the male component of the fastening tape attached to the front portion is joined to the fastener receiving part disposed at the back portion, after the tab portion of the fastening tape is spread out, for example.

Figure 3:
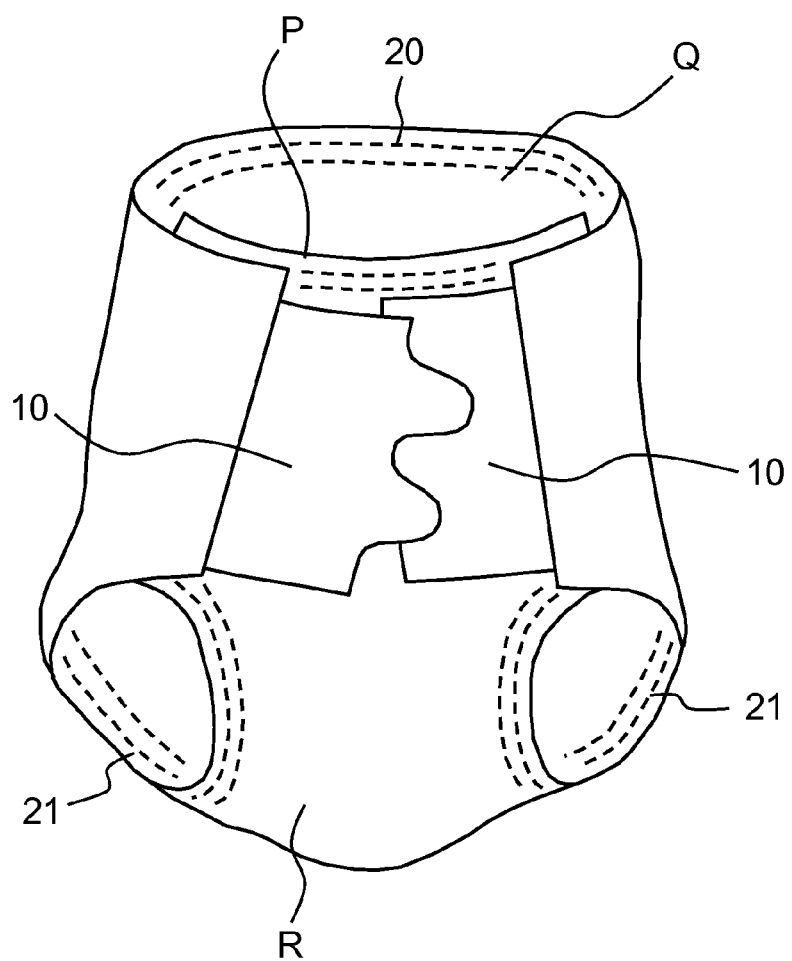
FIG. 3 shows an example of wearing a disposable diaper provided with a fastening tape of the present invention.

As described above, for the disposable diaper of the present invention, a pair of fastening tapes is preferably attached to the left and the right side edge portions of the front or back portion so that the surface with the male component of the fastening tape faces a wearer, and the fastener receiving part is preferably disposed on the outer surface of the back or front portion of the disposable diaper. Since the opposite surface of the surface with the male component of the tape substrate is embossed in the disposable diaper of the present invention, the male component of the fastening tape attached to the right side edge portion can be joined to the opposite surface of the surface with the male component of the tape substrate of the fastening tape attached to the left side edge portion in wearing the diaper, for example as shown in FIG. 3. This is because the embossed nonwoven fabric used in the opposite surface of surface with the male component of the tape substrate easily joins the male component of the hook-and-loop fastener. Since the disposable diaper has such a fastening tape, the adjustable range to the size around a wearer's waist expands, resulting in proper fastening of the fastening tape even when the waist of the wearer is so slim that the left and right fastening tapes overlap, for example.

Next, the material of each component of the disposable diaper of the present invention is explained. The top sheet is preferably composed of a liquid-permeable nonwoven fabric or the like, and the back sheet is preferably composed of a liquid-impermeable plastic film, a water-repellent nonwoven fabric, or the like.

The absorbent core can be obtained, for example, by the following steps of mixing a hydrophilic fiber assembly layer such as crushed pulp fiber, cellulose fiber and the like with a granular absorbent polymer resin to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, a hourglass shape, a center nipped-in gourd shape, a battledore shape, and the like.

A female component that can join the hook part of the male component is preferably used as the fastener receiving part, and a female component of the hook-and-loop fastener is exemplified as the female component, for example. A loop component is indicated as an example of the female component of the hook-and-loop fastener. The loop component is preferably made of a nonwoven fabric, a woven fabric, a knit, or a composite material of a plastic film having a nonwoven fabric, a woven fabric, or the like on a surface. The loop component preferably has a loop structure on the surface of each material. In addition, when the fastener receiving part is disposed on the outer surface of the disposable diaper and the outer surface of the back sheet or the outer pants sheet is composed of a nonwoven fabric, the back sheet and the outer pants sheet function as the fastener receiving part. Therefore, in this case, another component which functions as the fastener receiving part may not be employed.

A bonding means for bonding various components constituting the disposable diaper includes an adhesive agent, heat sealing, ultrasonic sealing, and the like. The adhesive agent includes a hot-melt adhesive such as a polyolefin based adhesive, a rubber based adhesive, a vinyl acetate based adhesive, and the like.

Figure 4:
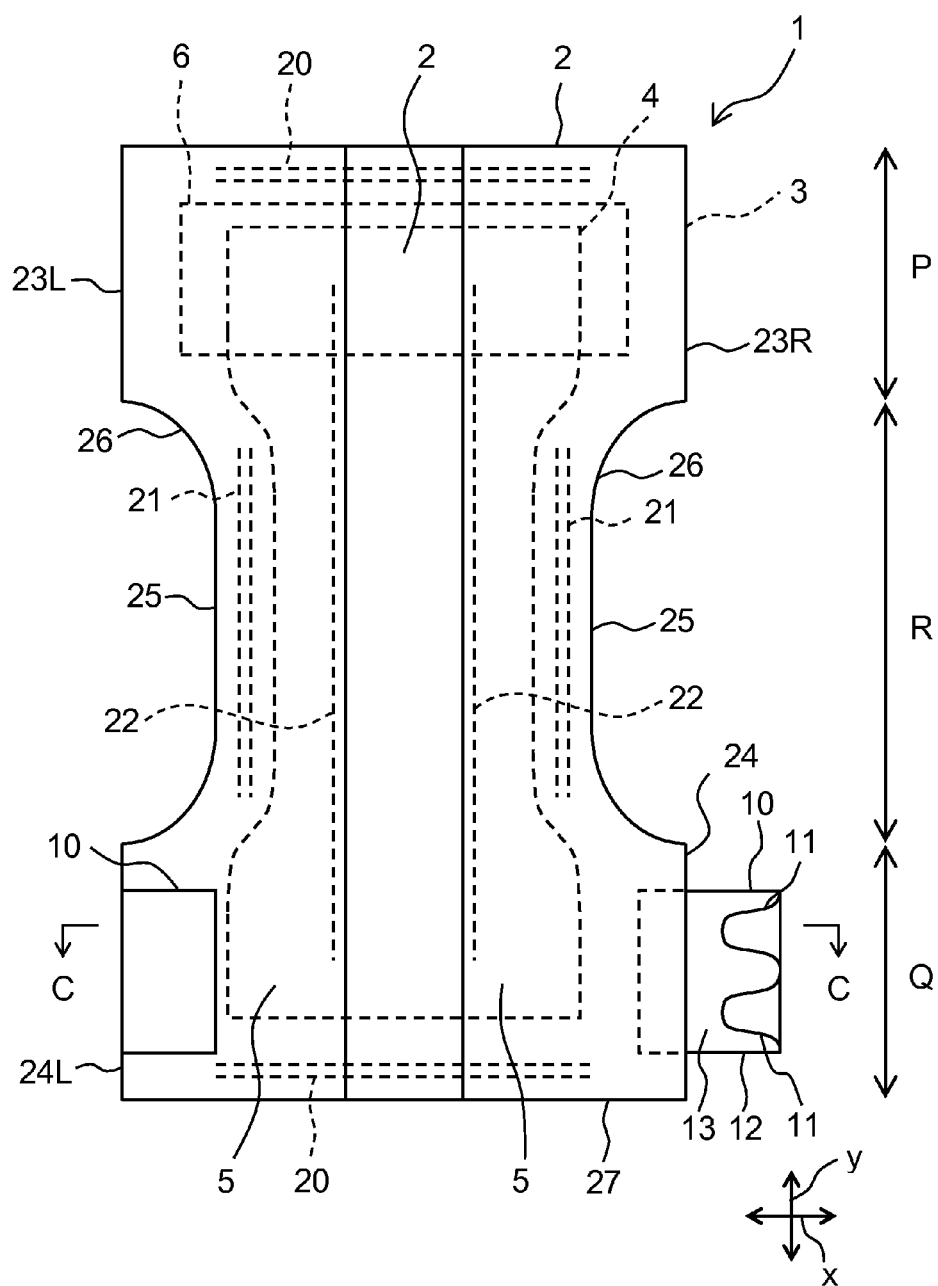
FIG. 4 shows an example of a disposable diaper provided with a fastening tape of the present invention.
Figure 5:
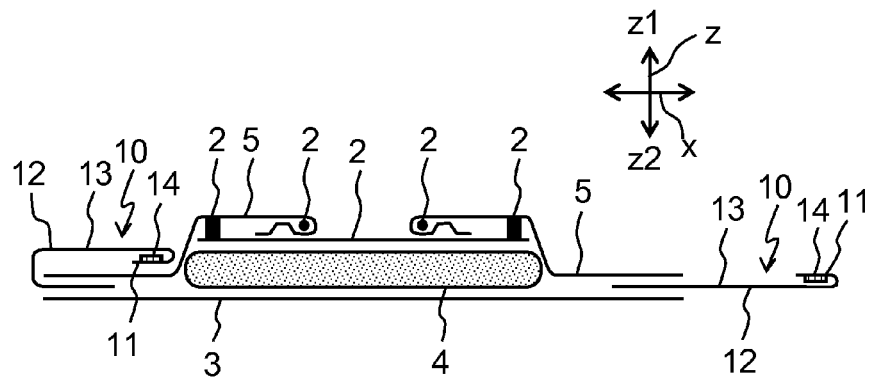
FIG. 5 shows a cross sectional view along line C-C in FIG. 4.

An example of the disposable diaper of the present invention is explained, referring to FIG. 4 and FIG. 5. FIG. 4 shows an example of the disposable diaper of the present invention, and FIG. 5 shows a cross sectional view along line C-C of FIG. 4. In FIG. 4 and FIG. 5, the arrow x direction is defined as a lateral direction (a width direction) and the arrow y direction is defined as a longitudinal direction (a lengthwise direction). The vertical direction with regard to the plane formed by the arrows x and y is defined as a vertical direction z (a thickness direction).

A disposable diaper 1 has a front portion P, a back portion Q and a crotch portion R therebetween. A leg cutout portion 26 is formed at the crotch portion R so that a wearer easily steps into the diaper.

The disposable diaper 1 has a laminated structure including a liquid-permeable top sheet 2, a liquid-impermeable back sheet 3 and an absorbent core 4 interposed between these sheets. The absorbent core 4 is centered on the crotch portion R and extends from the front portion P to the back portion Q. The top sheet 2 is disposed so as to faces the skin of a wearer's crotch, and allows excrement such as urine and the like to permeate through. The excrement that permeated the top sheet 2 is accommodated in the absorbent core 4. The back sheet 3 prevents the excrement from leaking outside, thereby protecting clothes and the like becoming soiled.

Side sheets 5, which extend in the longitudinal direction y, are provided on the left and the right side edge portions, with respect to the lateral direction x of the disposable diaper 1, of the top sheet 2. The top sheet 2 and the side sheets 5 are joined at side sheet fixing portions 28. Elastic components for erection 22 are provided on the internal edge portions, with respect to the lateral direction x, of the side sheets 5, respectively. When wearing the disposable diaper 1, the internal portions, with respect to the lateral direction x, of the side sheets 5 rise above the top sheet 2 (the z1 side of the vertical direction z), which is a direction toward the wearer's skin, by a shrinkage force of the elastic member for erection 22. This prevents excrement such as urine and the like from leaking outward with the lateral direction x. The side sheets 5 are preferably composed of a liquid-impermeable plastic film, a water-repellent nonwoven fabric, or the like, and more preferably composed of a water-repellent nonwoven fabric.

Leg elastic members 21 are attached on the left and the right side edge portions 25 of the crotch portion R of the disposable diaper 1 in a stretched state. Leg-gathers around a wearer's leg are formed by a shrinkage force of the leg elastic members 21, resulting in preventing excrement such as urine and the like from leaking from the crotch portion.

Waist elastic members 20 are attached on end portions 27, with respect to the longitudinal direction y, of the disposable diaper 1 in a stretched state. Waist-gathers around a wearer's waist are formed by a shrinkage force of the waist elastic members 20, resulting in preventing excrement such as urine and the like from leaking from a back side or an abdomen side.

A pair of the fastening tapes 10 are attached on a left side edge portion 24L and a right side edge portion 24R of the back portion Q so as to extend outward in the lateral directions x, and the fixing portion 12 of the fastening tape 10 is attached between the side sheets 5 and the back sheet 3. A fastener receiving part 6 is disposed at the front portion P. However, although it is not shown in FIG. 4, a pair of the fastening tape 10 may be attached on a left side edge portion 23L and a right side edge portion 23R of the front portion P so as to extend outward in the lateral directions x, and the fastener receiving part 6 may be disposed at the back portion Q.

In FIG. 4, the fastening tape 10 attached to the left side edge portion 24L (the left side in the Figure, and also the left side of a wearer in wearing) of the back portion Q is folded onto the internal surface of the disposable diaper main body, after the tab portion 11 is folded back and then the male component 14 of the tab portion 11 is joined to the fixing portion 12 of a tape substrate 13. In FIG. 4, the fastening tape 10 attached to the right side edge portion 24R (the right side in the Figure, and also the right side of the wearer in wearing) of the back portion Q extends outward from the disposable diaper main body in the lateral direction x, and the tab portion 11 is exposed in a state that the male component 14 joins the fixing portion 12 of the tape substrate 13. The disposable diaper 10 of unused and just manufactured has preferably in the state shown on the left side of FIG. 4.

To wear the disposable diaper 1, the male components 14 of the fastening tapes 10 are joined to the fastener receiving parts 6, after joining of the male components 14 to the tape substrates 13 are released and all the tab portions 11 on the left and the right side of the fastening tapes 10 are spread out. An example of wearing the disposable diaper 1 is shown in FIG. 3.

Next, a process for manufacturing a fastening tape of the present invention is explained. The fastening tape of the present invention is preferably manufactured by a process comprising the steps of: supplying a tape substrate made of a nonwoven fabric having one embossed surface (a tape supplying step: A-1 step); fixing a male component of a hook-and-loop fastener on the other surface of the tape substrate (a male component fixing step: A-2 step); folding back the tape substrate so that the male component is on the inner side (a folding back step: A-4 step); and pressing the whole area of the folded back male component to join the male component to the facing nonwoven fabric of the tape substrate (a male component joining step: A-5 step). The process for manufacturing a fastening tape of the present invention may also comprise a step of embossing one surface of a tape substrate made of a nonwoven fabric (an embossing step: A-1' step) instead of the tape supplying step (A-1 step).

At the tape supplying step (A-1 step), a tape substrate made of a nonwoven fabric having one surface that is embossed in advance is supplied.

When the embossing step (A-1' step) is provided instead of the tape supplying step (A-1 step), one surface of a tape substrate made of a nonwoven fabric having non-embossed both surfaces is embossed at the embossing step (A-1' step). Embossing can be conducted, for example, by pressing the tape substrate made of a nonwoven fabric with an embossing roll having a convexoconcaves roll surface and a flat roll having a smooth roll surface. A tape substrate with one embossed surface is obtained by the embossing step (A-1' step).

At the male component fixing step (A-2 step), a male component of a hook-and-loop fastener is fixed to the other surface of the tape substrate, that is the surface being not embossed of the tape substrate. The male component is fixed to the tape substrate in such a way that the surface without hooks is a surface to be fixed. The male component is fixed on the other surface of the tape substrate by the male component fixing step (A-2 step).

When the fastening tape is manufactured simultaneously two pieces as a pair, for example, a step of cutting the tape substrate and the male component at a cutting line crossing the male component may be provided (a tab portion cutting step: A-3 step). In this case, the male component of the hook-and-loop fastener is preferably provided on the part other than a pair of opposing ends of the tape substrate, and more preferably on the central part inward from the opposing ends at the male component fixing step (A-2 step).

At the folding back step (A-4 step), the tape substrate is folded back so that the male component is on the inner side. As a result, the male component becomes in facing relation to the surface being not embossed of the tape substrate. The tab portion is folded back at the boundary between the tab portion and the fixing portion so that the male component is on the inner side by the folding back step (A-4 step).

At the male component joining step (A-5 step), the whole area of the folded back male component is pressed to join the male component on the tab portion to the nonwoven fabric of the tape substrate which the male component faces. The male component on the tab portion is joined to the fixing portion of the tape substrate by the male component joining step (A-5 step).

With regard to the pressing, the whole area of the folded back male component is preferably pressed by a roll, and more preferably pressed by two rolls. The width of the roll is preferably greater than a length of a male component in a direction orthogonal to the direction of a roll movement. Pressing the male component by the roll enables almost uniform pressing of the whole area of the male component easily, resulting in allowing joining of the male component to a nonwoven fabric surface that is not embossed, which is difficult to join usually. As a result, releasing of the male component from the tape substrate and rejoining of the male component to other components or other places are prevented during the process for manufacturing of the fastening tape and the disposable diaper, resulting in preventing troubles easily in manufacturing. Further, the damage of the hook part of the male component and the damage to the fastening tape or the disposable diaper main body, which are pressed by the male component, are easily prevented in joining.

A roll for pressing may be a flat roll having a smooth roll surface or an embossing roll having a roll surface on which convexoconcaves are formed. When the embossing roll is used, the hook part of the male component can be pressed more deeply since the male component is locally pressed strongly, and therefore, the male component and the nonwoven fabric are firmly joined easily.

When two rolls are used for pressing, both rolls may be the flat rolls having a smooth roll surface. Also, one roll may be the embossing roll having a convexoconcaves roll surface and the other roll may be the flat roll. In this case, the embossing roll and the flat roll preferably press the whole area of the folded back male component so that the embossing roll meets the folded back tape substrate on the side which the male component is fixed.

As the embossing roll, a knurly embossing roll having a roll surface on which quadrangular pyramid shaped projections are formed in a matrix is preferably used. Since the knurly embossing roll can press the male component relatively uniformly with an appropriate strength, the male component and the nonwoven fabric are joined easily without damaging the hook part of the male component and the nonwoven fabric of the tape substrate pressed by the male component.

Figure 6A:
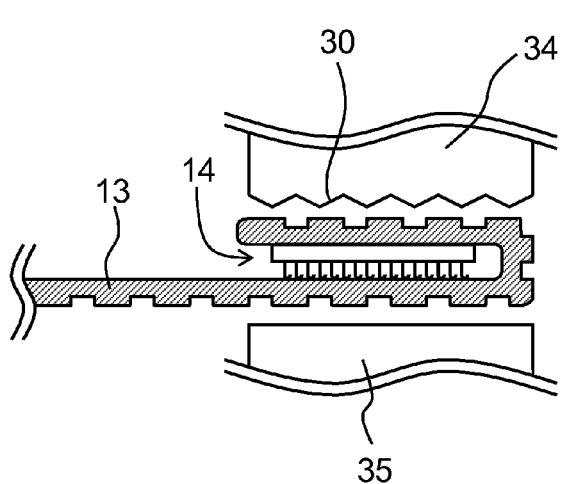
FIG. 6A shows a method for pressing a male component of a fastening tape of the present invention by an embossing roll to join a facing nonwoven fabric of a tape substrate.
Figure 6B:
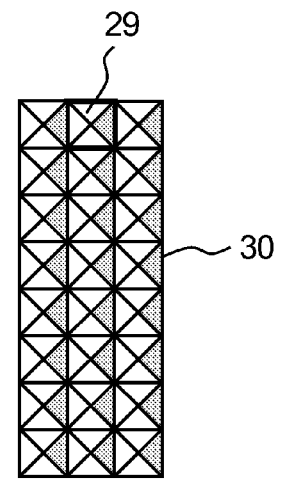
FIG. 6B shows an example of a roll surface of the embossing roll.

FIG. 6A shows a method for pressing the whole area of the folded back male component 14 by an embossing roll 34 and a flat roll 35 so that the embossing roll 34 meets the folded back tape substrate 13 on the side which the male component 14 is fixed. The embossing roll 34 has a roll surface (knurly embossings 30) on which quadrangular pyramid shape projections 29 are formed in a matrix as shown in FIG. 6B. Each quadrangular pyramid shaped projection 29 which constitutes the knurly embossings 30 has preferably the side length of a square or rectangle bottom in the range of from 0.1 mm to 3.0 mm and the height in the range of from 0.05 mm to 3.0 mm.

When the fastening tape is manufactured continuously, a step of cutting the tape substrate that the male component and the nonwoven fabric are joined (a fastening tape cutting step: A-6 step) is preferably provided after the male component joining step (A-5 step). At the fastening tape cutting step (A-6 step), the fastening tape manufactured continuously is cut, for example, by a cutter or the like to obtain one fastening tape.

A process for manufacturing a disposable diaper of the present invention preferably comprises the steps of: obtaining a disposable diaper main body having a front portion, a back portion and a crotch portion therebetween; obtaining the fastening tape manufactured by the process described above; and attaching the fastening tape to a side edge portion of the front or the back portion of a component constituting the disposable diaper main body. The disposable diaper of the present invention is manufactured by attaching the fastening tape obtained by the above manufacturing process to the disposable diaper main body.

The step of attaching the fastening tape to a component constituting the disposable diaper main body may be provided before or after the step of obtaining the disposable main body. Also, the step of obtaining the disposable main body may be divided into two steps, and the step of attaching the fastening tape to a component constituting the disposable diaper main body may be provided between the divided two steps.

Figure 7:
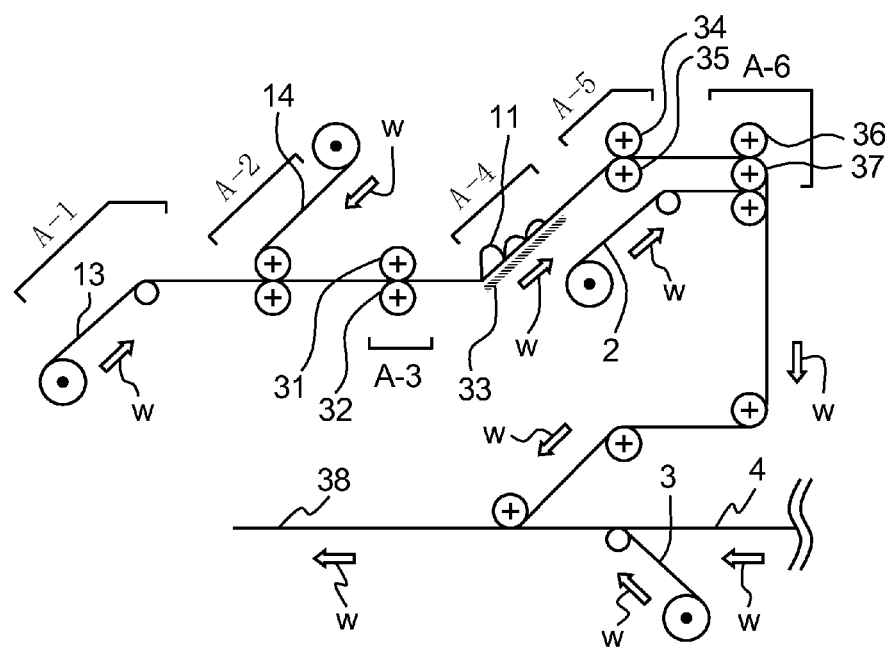
FIG. 7 shows an example of a process for manufacturing a fastening tape and a disposable diaper provided with the fastening tape of the present invention.

FIG. 7 shows a process for continuously manufacturing a fastening tape and a disposable diaper having the fastening tape. In FIG. 7, a fastening tape is manufactured by a process comprising the steps of a tape supplying step (A-1 step), a male component fixing step (A-2 step), a tab portion cutting step (A-3 step), a folding back step (A-4 step), a male component joining step (A-5 step), and a fastening tape cutting step (A-6 step). In FIG. 7, the fastening tape is manufactured simultaneously two pieces as a pair according to an arrow indicating a manufacturing direction w.

Figure 8:
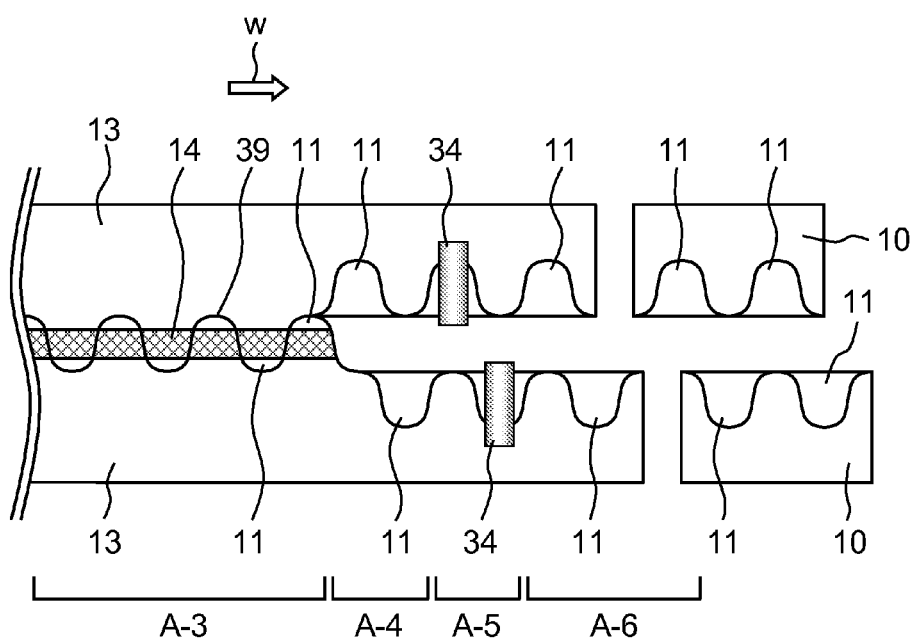
FIG. 8 shows an example of a process for manufacturing a fastening tape of the present invention.

FIG. 8 shows a drawing for easily understanding of the transition of manufacturing from the tab portion cutting step (A-3 step) to the fastening tape cutting step (A-6 step) of the process for manufacturing the fastening tape. In FIG. 8, the fastening tape is manufactured from left to right according to an arrow indicating the manufacturing direction w.

In the process for manufacturing the fastening tape, the tape substrate 13 made of a nonwoven fabric having one embossed surface is supplied at the tape supplying step (A-1 step). In FIG. 7, the tape substrate 13 made of a nonwoven fabric having the embossed lower surface is continuously reeled out from a roll body.

At the male component fixing step (A-2 step), the male component 14 of the hook-and-loop fastener is fixed on the other surface of the tape substrate 13. At the male component fixing step (A-2 step), the male component 14 is fixed on the non-embossed surface (upper surface in FIG. 7) of the tape substrate 13 at the center in the width direction. At this step, the male component 14 is fixed to the tape substrate 13 in such a way that the surface without hooks is a surface to be fixed. The width direction is the direction orthogonal to the direction the tape substrate 13 is supplied (the manufacturing direction w).

At the tab portion cutting step (A-3 step), the tape substrate 13 and the male component 14 are cut at a cutting line 39 crossing the male component 14. The tape substrate 13 and the male component 14 are cut by holding the tape substrate 13 and the male component 14 between a meandering line cutter 31 and an anvil roll 32 and bringing them out. In FIG. 8, the cutting line 39 meanders with crossing the male component 14 along the direction the tape substrate 13 is supplied (the manufacturing direction w), and forms the tab portion 11 composed of the tape substrate 13 and the male component 14. Here, the meandering cutting line 39 does not cross both edges, with respect to the width direction, of the tape substrate 13.

At the folding back step (A-4 step), the tape substrate 13 is folded back by a folding plate 33 so that the male component 14 is on the inner side. As a result, the male component 14 becomes to face the non-embossed surface of the tape substrate 13.

At the male component joining step (A-5 step), the whole area of the folded back male component 14 is pressed to join the male component 14 to the facing nonwoven fabric of the tape substrate 13. The male component 14 is joined to the facing nonwoven fabric of the tape substrate 13 by pressing the embossing roll 34 having a convexoconcaves roll surface and the flat roll 35. According to the present invention, since the male component 14 is joined to the facing nonwoven fabric in a process different from a process for manufacturing the disposable diaper main body, the disposable diaper main body is not damaged.

At the fastening tape cutting step (A-6 step), the tape substrate 13 that the male component 14 and the nonwoven fabric are joined is cut. At this step, the tape substrate 13 that the male component 14 is joined is cut by holding the tape substrate 13 between a separating cutter 36 and a transferring roll 37 and bringing it out the tape substrate 13, resulting in obtaining the fastening tape 10.

Next, the process for continuously manufacturing a disposable diaper provided with the fastening tape is explained, referring to FIG. 7.

The fastening tape obtained by the process for manufacturing a fastening tape is attached to the top sheet 2. The fastening tape is attached to the side edge portion of the front or the back portion of the top sheet 2.

The fastening tape may be attached to the top sheet 2 by the method of: temporarily placing the fastening tape on the upper surface of the top sheet so that the fixing portion of the fastening tape is located outside of the side edge portion of the top sheet 2; folding back the fixing portion onto the lower surface of the top sheet 2; and joining the fixing portion to the top sheet 2, for example. In this method, when the fastening tape is temporarily placed on the upper surface of the top sheet 2, the fastening tape may be temporarily bonded to the top sheet 2 by an adhesive or the like.

A component that the fastening tape is attached to is not limited to the top sheet, and the fastening tape may be attached to, for example, the back sheet, the side sheet or the outer pants sheet as a component of the disposable diaper main body. A component that the fastening tape is attached to is not limited particularly, as long as it is a component which constitutes the disposable diaper main body having the front portion, the back portion and the crotch portion therebetween.

The top sheet 2 which the fastening tape is attached to is further joined to the back sheet 3 provided with the absorbent core 4 to obtain a diaper sheet 38, resulting in obtaining the disposable diaper as a final product.

Industrial Applicability

The present invention relates to a fastening tape and a disposable diaper having the fastening tape. The present invention also relates to a process for manufacturing the fastening tape and a process for manufacturing the disposable diaper having the fastening tape.

The invention claimed is:

1. A fastening tape comprising
a tab portion formed at one end of a tape substrate made of a nonwoven fabric, and
a fixing portion formed at the other end of the tape substrate so as to be attached to a disposable diaper, wherein:
a male component of a hook-and-loop fastener is fixed to a surface of the tape substrate at the tab portion;
the second surface of the tape substrate, opposite to the first surface, is embossed at least at the fixing portion, and the first surface is not embossed;

the tab portion is folded back at the boundary between the tab portion and the fixing portion so that the male component is on the folded inner side; and the male component on the tab portion is joined to the fixing portion of the tape substrate.

2. The fastening tape according to claim 1, wherein the tape substrate is made of a spunbond nonwoven fabric having a weight per unit area in the range of from 30 g/m² to 100 g/m².

3. The fastening tape according to claim 1, wherein the male component on the tab portion is joined to the fixing portion by pressing the whole area of the male component against the fixing portion.

4. A disposable diaper comprising the fastening tape according to claim 1, wherein:

the disposable diaper has a front portion, a back portion and a crotch portion therebetween; and the fastening tape is attached to a side edge portion of the front or the back portion.

5. The fastening tape according to claim 1, wherein the male component of a hook-and-loop fastener includes hooks.

6. The fastening tape according to claim 1, wherein the second surface of the tape substrate forms an exterior surface of the tape substrate.

7. The fastening tape according to claim 1, wherein the second surface of the tape substrate is embossed so that the surface with the male component forms a shallow convecoconcaves.

8. The fastening tape according to claim 1, wherein the second surface of the tape substrate is entirely embossed.

9. A process for manufacturing a fastening tape comprising the steps in the following order of:

supplying a tape substrate made of a nonwoven fabric having one embossed surface;

fixing a male component of a hook-and-loop fastener on the other surface of the tape substrate which is not embossed;

folding back the tape substrate so that the male component is on the inner side; and pressing the whole area of the folded back male component to join the male component to the facing nonwoven fabric of the tape substrate.

10. The process for manufacturing a fastening tape according to claim 9, wherein the whole area of the folded back male component is pressed by a roll.

11. The process for manufacturing a fastening tape according to claim 6, wherein the whole area of the folded back male component is pressed by a flat roll and an embossing roll.

12. The process for manufacturing a fastening tape according to claim 9, wherein the whole area of the folded back male component is pressed by a flat roll and a knurly embossing roll.

13. A process for manufacturing a disposable diaper comprising the steps of:

obtaining a disposable diaper main body having a front portion, a back portion and a crotch portion therebetween;

obtaining a fastening tape manufactured by the process according to claim 9; and attaching the fastening tape to a side edge portion of the front or the back portion of a component constituting the disposable diaper main body.

14. A process for manufacturing a fastening tape comprising the steps in the following order of:

embossing one surface of a tape substrate made of a nonwoven fabric;

fixing a male component of a hook-and-loop fastener on the other surface of the tape substrate which is not embossed;

folding back the tape substrate so that the male component is on the inner side; and pressing the whole area of the folded back male component to join the male component to the facing nonwoven fabric of the tape substrate.

15. The process for manufacturing a fastening tape according to claim 14, wherein the whole area of the folded back male component is pressed by a roll.

16. The process for manufacturing a fastening tape according to claim 14, wherein the whole area of the folded back male component is pressed by a flat roll and an embossing roll.

17. The process for manufacturing a fastening tape according to claim 14, wherein the whole area of the folded back male component is pressed by a flat roll and a knurly embossing roll.

18. A process for manufacturing a disposable diaper comprising the steps of:

obtaining a disposable diaper main body having a front portion, a back portion and a crotch portion therebetween;

obtaining a fastening tape manufactured by the process according to claim 14; and attaching the fastening tape to a side edge portion of the front or the back portion of a component constituting the disposable diaper main body.

* * * * *